United States Patent [19]

Nishikawa et al.

[11] Patent Number: 5,719,173
[45] Date of Patent: Feb. 17, 1998

[54] METHOD FOR THE TREATMENT OF SCLEROSIS OF THE GLOMERULI

[75] Inventors: Kohei Nishikawa, Kyoto; Yumiko Shibouta, Suita; Keiji Kubo, Minoo, all of Japan

[73] Assignee: Takeda Chemical Industries, Ltd., Osaka, Japan

[21] Appl. No.: 696,475

[22] Filed: Aug. 14, 1996

Related U.S. Application Data

[62] Division of Ser. No. 229,930, Apr. 19, 1994.

[30] Foreign Application Priority Data

Apr. 22, 1993 [JP] Japan ......................... 5-095942

[51] Int. Cl.⁶ .............................................. A61K 31/41
[52] U.S. Cl. ........................................................ 514/381
[58] Field of Search ............................ 514/381, 394, 514/401

[56] References Cited

U.S. PATENT DOCUMENTS

| 5,128,356 | 7/1992 | Naka et al. | 514/381 |
| 5,196,444 | 3/1993 | Naka et al. | 514/381 |
| 5,250,554 | 10/1993 | Naka et al. | 514/381 |

FOREIGN PATENT DOCUMENTS

| 0 392 317 | 10/1990 | European Pat. Off. |
| 0 400 835 | 12/1990 | European Pat. Off. |
| 0 400 835 A1 | 12/1990 | European Pat. Off. |
| 0 425 921 A1 | 5/1991 | European Pat. Off. |
| 0 430 300 | 6/1991 | European Pat. Off. |
| 0 434 038 | 6/1991 | European Pat. Off. |
| 0 445 811 | 9/1991 | European Pat. Off. |
| 0 461 039 A1 | 11/1991 | European Pat. Off. |
| 0 591 136 | 12/1991 | European Pat. Off. |
| 0 483 683 | 5/1992 | European Pat. Off. |
| 0 518 033 | 12/1992 | European Pat. Off. |
| 0 520 423 | 12/1992 | European Pat. Off. |
| 0 588 299 A2 | 3/1994 | European Pat. Off. |
| 0 603 712 A2 | 6/1994 | European Pat. Off. |
| WO 92-00067 | 1/1992 | WIPO . |
| WO 92-04343 | 3/1992 | WIPO . |
| WO 92-10182 | 6/1992 | WIPO . |

OTHER PUBLICATIONS

Kohara et al. "Angiotensin Blockade and the Progression of Renal Damage in the Spontaneously Hypertensive Rat", *Hypertension*, 21,6:975–979 (1993).

Honma et al. "Renal protective effects of the angiotensin II(Ang II) receptor antagonist CV–11974 . . . ", *JASN*, 4:513 (1993).

Bohm et al. "The Angiotensin II Antagonist BIBR277 Normalized Blood Pressure and Improves . . . ", *The FASEB Jnl.*, 7,3:A246 (1993).

Wolf, et al. "Glucose–Induced Hypertrophy in Cultured Proximal Tubule Cells: Enhancement by Angeiotensin II (AII)", *The FASEB Jnl.*, 5,5:A1039 (1991).

Dunn "Prostaglandins, Angiotension II, and Proteinuria", *Nephron*, 5:30–37 (1990).

Noda et al. "Inhibition of Rabbit Aortic Angiotensin II (AII) Receptor by CV–11974, A New Nonpeptide AII Antagonist", *Bio. Pharm.*, 46,2:311–318 (1993).

*Primary Examiner*—Kevin E. Weddington
*Attorney, Agent, or Firm*—Foley & Lardner

[57] ABSTRACT

This invention relates to prophylactic or therapeutic drug for diabetic nephropathy or glomerulonephritis, comprising, as an active ingredient, a compound or salt thereof represented by general formula (I)

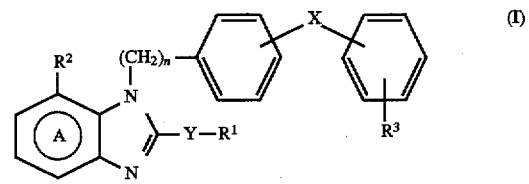

wherein $R^1$ stands for H or an optionally substituted hydrocarbon residue; $R^2$ stands for an optionally esterified carboxyl group; $R^3$ stands for a group actually or potentially capable of forming an anion; X shows that the phenylene and phenyl groups bind to each other directly or through a spacer having an atomic chain length of two or less; n stands for 1 or 2; ring A stands for a benzene ring having an optional substituent in addition to $R^2$; Y stands for a bond, —O—, —S(O)$_m$— (wherein m stands for 0, 1 or 2), or —N($R^4$)— (wherein $R^4$ stands for H or an optionally substituted alkyl group).

1 Claim, No Drawings

5,719,173

METHOD FOR THE TREATMENT OF SCLEROSIS OF THE GLOMERULI

This application is a division of application Ser. No. 08/229,930, filed Apr. 19, 1994.

FIELD OF THE INVENTION

This invention relates to a prophylactic or therapeutic drug containing an angiotensin II antagonistic compound or salt thereof as the active constituent, for diabetic nephropathy or glomerulonephritis.

BACKGROUND OF THE INVENTION

The kidneys are a major target organ of hypertension. Prolonged hypertension induces various renal impairments, mainly through renovascular lesions. Among them, contraction of renal vessels and degenerative lesions of elastic fibers lead to further elevation of the blood pressure. It is generally believed that hypertension raises renal intraglomerular pressure, which overloads the glomeruli, stimulating fibrosis and enlargement of the mesangial region, which advances to hardening of the glomeruli. In diabetic nephropathy as well, elevation in intraglomerular pressure is followed by trace albuminuria, progressing to the sclerosis of the glomeruli. Eventually, renal functions decline, resulting in chronic renal failure requiring artificial dialysis therapy. In recent years, 20% of patients with end-stage renal failure who commence artificial dialysis have diabetic nephropathy as the underlying disease. The number of patients likely to receive artificial dialysis tends to increase year after year, posing a critical problem in the medical care system. At present, it is said that there are few ideal pharmaceutical therapies for chronic renal failure, and even that blood-pressure-lowering therapy may aggravate rather than improve renal failure.

Angiotensin II antagonistic compounds are known as a therapeutic drug for cardiovascular diseases, e.g., hypertension, cardiac diseases (heart enlargement, heart failure, myocardial infarction, etc.), apoplexy, nephritis, etc. (European Patent Official Gazette (EPO) 459136A). The mechanism of their action is considered to be based on inhibition of binding to the angiotensin II receptor of angiotensin II, which possesses intense vasoconstrictive action. EP 459136A$_1$ describes the availability of angiotensin II antagonists in the treatment of nephropathy or nephritis.

Many data of clinical and experimental studies have been reported on the relation between renal diseases and hypertension. It is now established that the kidneys are directly or indirectly involved in the onset of hypertension, and also are apt to be affected by hypertension. However, hypertension in chronic glomerulonephritis has been poorly elucidated, particularly as to causative factors, effects of hypertension on the course of nephritis, and prophylactic effects of blood pressure lowering therapy.

Currently, nephritis is considered to be a clinical picture of different diseases with different entities. In accordance with the popularization of renal biopsy, renal diseases have been reviewed, resulting in their redefinition as a wide range of diseases characterized by proteinuria ("Shibata's Internal Medicine of the Kidneys," by Seiichi Shibata, Bunkodo, 1988). Glomerulonephritis, once regarded as a single disease, has been differentiated into glomerulonephritis, chronic pyelonephritis, IgA nephropathy, periarteritis nodosa, gout, diabetes, systemic lupus erythematosus (SLE), hepatic infarction, hereditary renal disease, amyloidosis, and Wegener's sarcoma.

Diabetes associated with hypertension facilitates cardiovascular impairment and/or other organ complications, greatly affecting life expectancy. Accordingly, it is important to control blood pressure within the normal range during treatment, along with the control of diabetes and the improvement or prevention of arteriosclerosis.

OFJECT OF THE INVENTION

This invention provides a prophylactic or therapeutic drug for diabetic nephropathy or glomerular nephritis.

SUMMARY OF THE INVENTION

Under the above-mentioned circumstances, the inventors intensively studied to develop a drug for the prophylaxis or treatment of nephropathy or nephritis. Ultimately, they found that compounds possessing angiotensin II antagonistic action, represented by a particular structural formula, are very effective in the prophylaxis or treatment of diabetic nephropathy or glomerulonephritis. The present invention was thus accomplished.

Namely, this invention relates to a prophylactic or therapeutic drug for diabetic nephropathy or glomerulonephritis, containing, as the active constituent, a compound or salt thereof represented by formula (I):

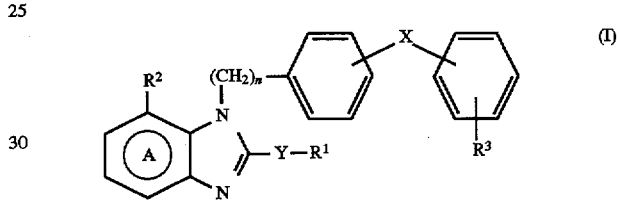

(wherein $R^1$ stands for H or an optionally substituted hydrocarbon residue; $R^2$ stands for an optionally esterified carboxyl group; $R^3$ stands for a group actually or potentially capable of forming an anion; X shows that the phenylene and phenyl groups bind to each other directly or through a spacer having an atomic chain length of two or less; n stands for 1 or 2; ring A stands for a benzene ring having one or two optional substituents in addition to $R^2$; Y stands for a bond, —O—, —S(O)$_m$— (wherein m stands for 0, 1 or 2), or —N($R^4$)— (wherein $R^4$ stands for H or an optionally substituted alkyl group)).

DETAILED DESCRIPTION OF THE INVENTION

The invented compounds used for prophylactic or therapeutic purposes, as represented by formula (I), are structurally very prominently characterized by the coexistence of $R^2$, standing for an optionally esterified carboxyl group, and $R^3$, standing for a group actually or potentially capable of forming an anion. This structural characteristic contributes to the onset of very intense prophylactic or therapeutic effect on diabetic nephropathy or glomerulonephritis.

The compounds of this invention, possessing angiotensin II antagonistic action, represented by formula (I), can be favorably used in the prophylaxis or treatment of diabetic nephropathy or glomerulonephritis.

In formula (I), $R^1$ stands for H or an optionally substituted hydrocarbon residue.

Examples of the hydrocarbon residue represented by $R^1$ include alkyl, alkenyl, alkynyl, cycloalkyl, aryl and aralkyl groups. Among them alkyl, alkenyl and cycloalkyl groups are preferable.

The alkyl group represented by $R^1$ is a straight chain or branched lower alkyl group having 1 to about 8 carbon atoms, as exemplified by methyl, ethyl, propyl, isopropyl, butyl, isobutyl, sec-butyl, t-butyl, pentyl, i-pentyl, hexyl, heptyl or octyl.

The alkenyl group represented by $R^1$ is a straight chain or branched lower alkenyl group having 2 to about 8 carbon atoms, as exemplified by vinyl, propenyl, 2-butenyl, 3-butenyl, isobutenyl or 2-octenyl.

The alkynyl group represented by $R^1$ is a straight chain or branched lower alkynyl group having 2 to about 8 carbon atoms, as exemplified by ethynyl, 2-propinyl, 2-butynyl, 2-pentynyl or 2-octynyl.

The cycloalkyl group represented by $R^1$ is a lower cycloalkyl group having 3 to about 6 carbon atoms, as exemplified by cyclopropyl, cyclobutyl, cyclopentyl or cyclohexyl.

The above mentioned alkyl, alkenyl, alkynyl or cycloalkyl group may optionally be substituted with hydroxyl group, an optionally substituted amino group (e.g. amino, N-lower ($C_{1-4}$) alkylamino or N,N-dilower ($C_{1-4}$) alkylamino), halogen, a lower ($C_{1-4}$) alkoxy group, a lower ($C_{1-4}$) alkylthio group.

The aralkyl group represented by $R^1$ is, for example, a phenyl-lower ($C_{1-4}$) alkyl such as benzyl or phenethyl, and the aryl group represented by $R^1$ is, for example, phenyl.

The above mentioned aralkyl or aryl group may optionally have, on any position of its benzene ring, for example, halogen (e.g. F, Cl or Br), nitro, an optionally substituted amino group (e.g. amino, N-lower ($C_{1-4}$) alkylamino or N,N-dilower ($C_{1-4}$) alkylamino), lower ($C_{1-4}$) alkoxy (e.g. methoxy or ethoxy), lower ($C_{1-4}$) alkylthio (e.g. methylthio or ethylthio) or lower ($C_{1-4}$) alkyl (e.g. methyl or ethyl).

Among the above mentioned groups represented by $R^1$, optionally substituted alkyl, alkenyl or cycloalkyl groups (e.g. a lower ($C_{1-5}$) alkyl, lower ($C_{2-5}$) alkenyl or lower ($C_{3-6}$) cycloalkyl group optionally substituted with hydroxyl group, amino group, halogen or a lower ($C_{1-4}$) alkoxy group) are preferable.

Y stands for a bond, —O—, —S(O)$_m$— (wherein m is 0, 1 or 2) or —N($R^4$)— (wherein $R^4$ is hydrogen or an optionally substituted lower alkyl group). Y is preferably a bond, —O—, —S— or —N($R^4$)— (wherein $R^4$ is hydrogen or a lower ($C_{1-4}$) alkyl group (e.g. methyl, ethyl, propyl, isopropyl, butyl, sec-butyl, t-butyl)).

With respect to formula (I) above, the group for $R^3$, capable of forming an anion (a group having a hydrogen atom capable of leaving as a proton), or a group capable of changing thereto, is exemplified by 5- to 7- membered (preferably 5- or 6- membered) monocyclic heterocyclic ring residues which contain one or more of N, S and O and which may be substituted (preferably N-containing heterocyclic residues having a hydrogen atom capable of leaving as a proton), and groups capable of changing thereto in vivo. Such groups include the following:

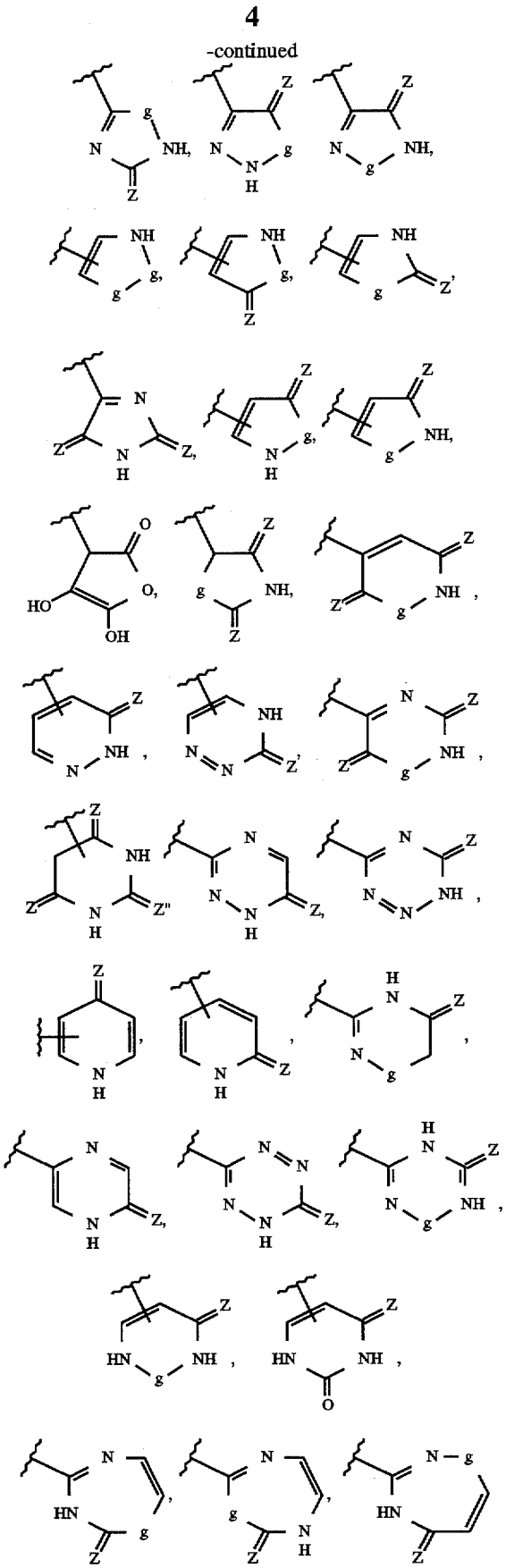

The chemical bond between the group for R³ and the partner phenyl group may be a carbon-carbon bond as shown above, or a nitrogen-carbon bond via one of the several nitrogen atoms when the symbol g stands for —NH— in the above formulas. For instance, when R³ is represented by

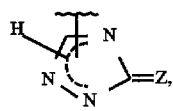

embodiments are

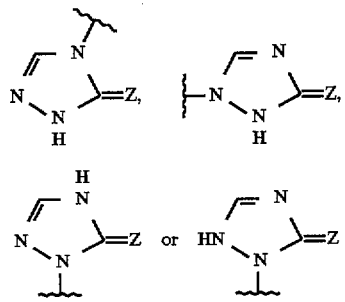

Other R³ examples binding through the nitrogen atom are

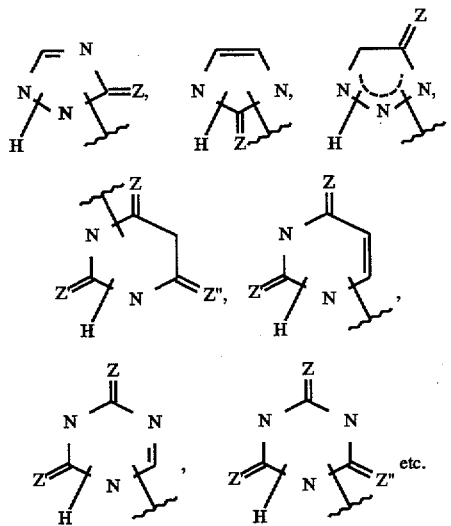

In the above groups, g stands for —CH₂—, —NR⁷—, oxygen atom, or

>=Z, >=Z', and >=Z" each stand for a carbonyl group, a thiocarbonyl group or an optionally oxidized sulfur atom (e.g., S, S(O), S(O)₂) (preferably, a carbonyl or thiocarbonyl group; more preferably, a carbonyl group); m stands for the integer 0, 1 or 2; R⁷ stands for a hydrogen atom or an optionally substituted lower alkyl group (e.g. a lower ($C_{1-4}$) alkyl group (e.g. methyl, ethyl, propyl, isopropyl, butyl, sec-butyl, t-butyl)).

Preferable examples of R³ include 2,5-dihydro-5-oxo-1, 2,4-oxadiazole ring residue, 2,5-dihydro-5-thioxo-1,2,4-oxadiazole ring residue or 2,5-dihydro-5-oxo-1,2,4-thiadiazole ring residue having —NH or —OH group as proton donor and carbonyl group, thiocarbonyl group or sulfinyl group as proton acceptor simulateneously.

And, while the heterocyclic residue represented by R³ may form a condensed ring by connecting the substituents on the ring, it is preferably a 5- to 6- membered ring, more preferably a 5-membered heterocyclic residue. Especially groups represented by the formula

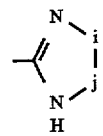

wherein i stands for —O— or —S—; j stands for >C=O, >C=S or >S(O)$_m$; m stands for the integer 0, 1 or 2 (in particular, 2,5-dihydro-8-oxo-1,2,4-oxadiazole-3-yl; 2,5-dihydro-5-thioxo-1,2,4-oxadiazole-3-yl; 2,5-dihydro-5-oxo-1,2,4-thiadiazole-3-yl) are preferable. R³ can be substituted at the ortho, meta or para position, most preferably at the ortho position.

In addition, the above-mentioned heterocyclic residue (R³) have the following tautomeric isomers:

In

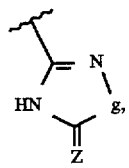

when Z=0, and g=0

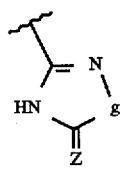

the three tautomeric isomers a, b and c exist.

The heterocyclic residue represented by the above formula comprises all of these a, b and c.

Moreover, R³ may be a carboxyl group, tetrazolyl group, trifluoromethanesulfonamide group (—NHSO₂CF₃), phosphate group, sulfonic group, cyano group, or lower ($C_{1-4}$) alkoxycarbonyl group; these groups each may be protected by an optionally substituted lower alkyl or acyl group. Any group capable of forming an anion biologically or physiologically (e.g. through biological reactions such as oxidation, reduction or hydrolysis caused by enzymes in the body) or chemically, or a group capable of changing thereto is acceptable.

As R³, a tetrazolyl or carboxyl (preferably tetrazolyl) group optionally protected by an optionally substituted lower ($C_{1-4}$) alkyl (e.g., methyl, triphenylmethyl, methoxymethyl, ethoxymethyl, p-methoxybenzyl, p-nitrobenzyl, etc.) or acyl (e.g., lower ($C_{2-5}$) alkanoyl, benzoyl, etc.) group is preferable. $R^3$ can be replaced at the ortho, meta or para position, most preferably at the ortho position.

X stands for a covalent bond between the 2 phenyl rings or a spacer having a chain length of 1 to 2 atoms as the linear moiety between the adjoining phenylene group and phenyl group. Preferably, X is a covalent bond. The spacer having a chain length of 1 to 2 atoms may consist of a divalent chain in which the number of atoms composing the straight chain portion is either 1 or 2, and may have a side chain. For example, a lower ($C_{1-4}$) alkylene, —CO—, —O—, —S—, —NH—, —CO—NH—, —O—$CH_2$—, —S—$CH_2$—, —CH=CH—, etc. are listed.

n stands for the integer 1 or 2 (preferably 1).

The formula represented by the above-mentioned $R^3$, X and n:

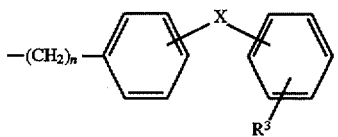

is preferably represented by the formula:

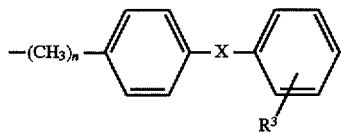

$R^2$ in formula (I) is an optionally esterified carboxyl group.

The optionally esterified carboxyl group as $R^2$ includes the group represented by the formula —CO—D [wherein D stands for a hydroxyl group or an optionally substituted alkoxyl group {e.g., a lower ($C_{1-6}$) alkoxyl group whose alkyl portion is optionally substituted with a hydroxyl, optionally substituted amino (e.g., amino, dimethylamino, diethylamino, piperidino, molphorino, etc.), halogen, lower ($C_{1-6}$) alkoxyl, lower ($C_{1-6}$) alkylthio or optionally substituted dioxolanyl (e.g., 5-methyl-2-oxo-1,3-dioxolane-4-yl, etc.) group, or the group represented by the formula —O—CH($R^6$)—OCOR$^5$ [wherein $R^6$ stands for H, a lower ($C_{1-6}$) straight chain or branched alkyl group (e.g., methyl, ethyl, n-propyl, isopropyl, n-butyl, isobutyl, t-butyl, n-pentyl, isopentyl neopentyl, etc.), a lower ($C_{2-6}$) straight chain or branched alkenyl group or a lower ($C_{3-8}$) cycloalkyl group (e.g., cyclopentyl, cyclohexyl, cycloheptyl, etc.); $R^5$ stands for a lower ($C_{1-6}$) straight chain or branched alkyl group (e.g., methyl, ethyl, n-propyl, isopropyl, n-butyl, isobutyl, sec-butyl, t-butyl, n-pentyl, isopentyl, neopentyl, etc.), a lower ($C_{2-6}$) straight chain or branched alkenyl group, a lower ($C_{3-8}$) cycloalkyl group (e.g., cyclopentyl, cyclohexyl, cycloheptyl, etc.), a lower ($C_{1-3}$) alkyl group substituted with $C_{3-8}$ cycloalkyl (e.g. cyclopentyl, cyclohexyl, cycloheptyl) or an optionally substituted aryl group such as phenyl group (e.g., benzyl, p-chlorobenzyl, phenetyl, cyclopentylmethyl, cyclohexylmethyl, etc.), a lower ($C_{2-3}$) alkenyl group optionally substituted with $C_{3-8}$ cycloalkyl or an optionally substituted aryl group such as phenyl (e.g., cinnamyl, etc. having alkenyl moiety such as vinyl, propenyl, allyl and isopropenyl, etc.), an aryl group such as optionally substituted phenyl (e.g., phenyl, p-tolyl, naphtyl, etc.), a lower ($C_{1-6}$) straight chain or branched alkoxyl group (e.g., methoxyl, ethoxyl, n-propoxyl, isopropoxyl, n-butoxyl, isobutoxyl, sec-butoxyl, t-butoxyl, n-pentyloxyl, isopentyloxyl, neopentytoxyl, etc.), a lower ($C_{2-8}$) straight chain or branched alkenyloxyl group (e.g., allyloxyl, isobutenyloxyl, etc.), a lower ($C_{3-8}$) cycloalkyloxyl group (e.g., cyclopentytoxyl, cyclohexyloxyl, cycloheptyloxyl, etc.), a lower ($C_{1-3}$) alkoxyl group substituted with a $C_{3-8}$ cycloalkyl (e.g., cyclopentyl, cyclohexyl, cycloheptyl, etc.) or an aryl group such as optionally substituted phenyl (e.g., benzyloxy, phenethyloxy, cyclopentylmethyloxy and cyclohexyhnethyloxy having alkoxy moiety such as methoxy, ethoxy, n-propoxy and isopropoxy), a lower ($C_{2-3}$) lower alkenyloxy group substituted with a $C_{3-8}$ cycloalkyl (e.g., cyclopentyl, cyclohexyl, cycloheptyl, etc.) or an optionally substituted aryl group such as phenyl group (e.g., cinnamyloxy etc. having alkenyloxy moiety such as vinyloxy, propenyloxy, allyloxy, isopropenyloxy, etc.), or an optionally substituted aryloxyl group such as phenoxyl (e.g., phenoxyl, p-nitrophenoxyl, naphtoxyt, etc.,)}]. The substituent for $R^2$ may be a group actually or potentially capable of forming an anion [e.g., tetrazolyl group, trifluoromethanesulfonamide group, phosphate group or sulfonic group optionally protected by an alkyl {e.g., lower ($C_{1-4}$) alkyl, etc.} or acyl {e.g., lower ($C_{2-5}$) alkanoyl, optionally substituted benzoyl, etc.} group].

For example, the following substituents are listed: —COOH and its salts, —COOMe, —COOEt, —COOtBu, —COOPr, pivaloyloxymethoxycarbonyl, 1-(cyclohexyloxycarbonyloxy)ethoxycarbonyl, (5-methyl-2-oxo-1,3-dioxolane-4-yl)methoxycarbonyl, acetoxymethoxycarbonyl, propionyloxymethoxycarbonyl, n-butylyloxymethoxycarbonyl, isobutylytoxymethoxycarbonyl, 1-(ethoxycarbonyloxy) ethoxycarbonyl, 1-(acetoxy)ethoxycarbonyl, 1-(isobutylyloxy)ethoxycarbonyl, cyclohexytcarbonyloxymethoxycarbonyl, benzoyloxymethoxycarbonyl, cinnamiloxycarbonyl and cyclopentylcarbonyloxymethoxycarbonyl, etc. Furthermore, $R^2$ may be any of the groups actually or potentially capable of forming an anion (e.g., $COO^-$ or its derivatives, etc.) under biologic, or physiologic, conditions (e.g., oxidation or reduction induced by an enzyme present in the living body; in vivo reaction such as hydrolysis) or chemically. $R^2$ may also be a carboxyl group or its prodrug. $R^2$ may be a group capable of being biologically or chemically biotransformed to an anion.

Among the groups described as $R^2$, preferable ones include carboxyl, esterified carboxyl (e.g. methyl ester, ethyl ester or an ester formed by binding of a group represented by the above mentioned formula —O—CH($R^6$)—OCOR$^5$ to carbonyl) and optionally protected tetrazolyl, carboaldehyde and hydroxymethyl.

In general formula (I), ring A may have, in addition to the group represented by $R^2$, another substituent, e.g., a halogen atom (e.g., F, Cl, Br, etc.), cyano group, nitro group, lower ($C_{1-4}$) alkyl group, lower ($C_{1-4}$) alkoxyl group, optionally substituted amino group {e.g., amino, N-lower ($C_{1-4}$) alllkylamino (e.g., methylamino, etc.), N,N-dilower ($C_{1-4}$) alkylamino (e.g., dimethylamino, etc.), N-arylamino (e.g., phenylamino, etc.), alicyclic amino (e.g., morpholino, piperidino, piperazino, N-phenylpiperazino, etc.), etc.}, a group represented by the formula—CO—D' [wherein D' stands for a hydroxyl group or a lower ($C_{1-4}$) alkoxyl group whose alkyl moiety may be substituted with a hydroxyl group, lower ($C_{1-4}$) alkoxyl group, lower ($C_{2-6}$) alkanoyloxy (e.g., acetoxyl, pivaloytoxyl, etc.) or lower ($C_{1-6}$) alkoxycarbonyloxyl (e.g., methoxycarbonyloxyl, ethoxycarbonyloxy, cyclohexyloxycarbonyloxy, etc.) group], or tetrazolyl, trifluoromethanesulfonamide, phosphoric acid or sulfonic acid group which may be protected by lower ($C_{1-4}$) alkyl or acyl group (e.g., lower ($C_{2-5}$) alkanoyl, optionally substituted benzoyl, etc.); among them, a lower ($C_{1-4}$) alkyl group and a halogen group are preferable. Of these substituents, one or two may simultaneously substitute for groups at available positions in the ring.

Among the compounds represented by the above mentioned formula (I), compounds represented by formula (I') are preferred:

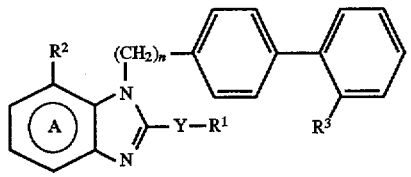

[wherein ring A stands for a benzene ring which may have another 1 or 2 substituents in addition to the group represented by $R^2$; $R^1$ stands for H or an optionally substituted lower ($C_{1-6}$) alkyl (preferably lower ($C_{1-4}$) alkyl); Y stands for O, N(H) or S; $R^2$ is a group represented by the formula —CO—D" [wherein D" stands for hydroxyl group, or a lower ($C_{1-4}$) alkoxy whose alkyl moiety is optionally substituted with hydroxyl group, amino, halogen, a lower ($C_{2-6}$) alkanoyloxy (e.g. acetyloxy and pivaloyloxy, etc.), lower ($C_{4-7}$) cycloalkanoyloxy, lower ($C_{1-6}$) alkoxycarbonyloxy (e.g. methoxycarbonytoxy, ethoxycarbonyloxy), lower ($C_{3-7}$) cycloalkoxycarbonyloxy (e.g. cyclohexyloxycarbonyloxy) or a lower ($C_{1-4}$) alkoxy; $R^3$ stands for a tetrazolyl, carboxyl group or groups represented by the formula,

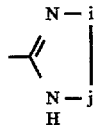

wherein i stands for —O— or —S—; j stands for >C=O, >C=S or >S(O)$_m$; and m is of the same meaning as defined above, which are optionally protected with optionally substituted lower ($C_{1-4}$) alkyl (e.g. methyl, triphenylmethyl, methoxymethyl, acetyloxymethyl, methoxycarbonyloxymethyl, ethoxycarbonyioxymethyl, 1-(cyclohexyloxycarbonyloxy)ethyl and pivaloyloxymethyl, etc.) or an acyl group (e.g. a lower $C_{2-5}$ alkanoyl and benzoyl, etc.).; n is 1 or 2.

In the formula (I'), substituents on the optionally substituted lower alkyl for $R^1$ include a hydroxyl group, an amino group, halogen and a lower ($C_{1-4}$) alkoxy group.

In the formula (I'), ring A is a benzene ring which may have a substituent, in addition to the group $R^2$, such as a halogen (e.g., F, Cl, Br), lower ($C_{1-4}$) alkyl, lower ($C_{1-4}$) alkoxy, nitro, a group represented by the formula —CO—D', wherein D' represents a hydroxyl group or a lower ($C_{1-4}$) alkoxy whose alkyl moiety may be substituted with a hydroxyl group, lower ($C_{1-4}$) alkoxy, lower ($C_{2-6}$) alkanoyloxy (e.g., acetoxy, pivaloyloxy, etc.) or lower ($C_{1-6}$) alkoxycarbonyloxy (e.g., methoxycarbonyloxy, ethoxycarbonyloxy, cyclohexyloxycarbonytoxy), or an amino which may be substituted with a lower ($C_{1-4}$) alkyl (preferably a substituent such as a lower ($C_{1-4}$) alkyl or halogen). More preferably, A is a benzene ring which has no substituent in addition to the group represented by the formula $R^2$.

As the salt thereof, pharmaceutically acceptable salts are used, e.g., a salt with an inorganic base, organic base, inorganic acid, organic acid, or basic or acidic amino acid. Inorganic bases appropriate to form the salt include alkali metals such as sodium and potassium, alkali soil metals such as calcium and magnesium, aluminum and ammonium. Organic bases appropriate to form the salt include trimethylamine, triethylamine, pyridine, picoline, ethanolamine, jetanolamine, triethanolamine, dicyclohexylamine, and N,N'-dibenzylethylenediamine. Inorganic acids appropriate to form the salt include hydrochloric acid, hydroboric acid, nitric acid, sulfuric acid, and phosphoric acid. Organic acids appropriate to form the salt include formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. Basic amino acids to form the salt include arginine, lysine and ornithine. Acidic amino acids to form the salt include aspartic acid and glutamic acid.

As an active ingredient of the present invention, the compounds described in the Examples of Japan Provisional Publication No. 364171/1992 and EP520423 are preferred.

The compounds represented by general formula (I) were, for instance, disclosed in Provisional Publication Nos. 9373/1999 and 364171/1999, and EP590423, and can be manufactured as described in these publications.

Compound (I) or salts thereof possessing angiotensin II antagonistic action referred to in the present invention are of sufficiently low toxicity to be used as a pharmaceutical for animals, particularly mammals (e.g., humans, dogs, rabbits, rats, mice, etc.), in the prophylaxis or treatment of diabetic nephropathy or glomerulonephritis.

Compound (I) or salts thereof represented by general formula (I) can be administered by the oral route, non-oral route, inhalation, rectal injection, or topical administration, as pharmaceutical constituents or preparations (e.g., powder, granules, tablets, pills, capsules, injection, syrup, emulsion, elixir, suspension, solution, etc.). At least one compound of the present invention can be used singly or in mixture with a carrier allowable as a pharmaceutical (adjuvant, vehicle, supportive agent, and/or diluting agent).

The constituents of a pharmaceutical can be prepared according to the usual manner. In the present specification, the non-oral route includes subcutaneous injection, intravenous injection, intramuscular injection, peritoneal injection and intravenous drip. For prescription injection, sterile aqueous or oily suspensions for injection can be prepared by using an appropriate emulsifier or humidifier and a suspending agent, according to known methods. The sterile prescription agent for injection may be a non-toxic, non-orally administrable diluting agent such as aqueous solution or a sterile injectable solution or suspension in a solvent. As the usable vehicle or solvent, water, Ringer's solution, isotonic saline, etc. are allowed; as an ordinary solvent, or suspending solvent, sterile involatile oil can be used. For these purposes, any kind of involatile oil and fatty acid can be used, including natural or synthetic or semisynthetic fatty oils or fatty acids; natural or synthetic or semisynthetic mono- or di- or tri-glycerides.

The suppository for rectal administration can be manufactured via a particular process, in which the drug is mixed with an appropriate, non-irritant supporting agent, e.g., cocoa butter or polyethylene glycol, that is solid at normal temperature but liquid at intestinal temperature and therefore melts in the rectum to release the drug.

As the solid-type dosage form for oral administration, powder, granules, tablets, pills and capsules are listed as mentioned above. In these dosage forms, the active constituent compound can be mixed with at least one additive, including sucrose, lactose, cellulose, mannitol, maltitol, dextran, starches, agar, arginates, chitins, chitosans, pectins, gum tragacanth, gum arabic, gelatin, collagen, casein, albumin, synthetic or semisynthetic polymer, and glyceride. These dosage forms can also contain other type(s) of additives, e.g., inactive diluting agent, lubricant such as magnesium stearate, paraben, preserving agent such as sorbic acid, ascorbic acid, α-tocopherol, antioxidant such as cysteine, disintegrator, binder, thickener, buffering agent, sweetening agent, flavoring agent, performing agent, etc. Tablets and pills can be further processed into enteric coated preparations. The liquid preparations for oral administration include emulsion, syrup, elixir, suspension and solution preparations allowable for medical use. These preparations may contain inactive diluting agents ordinarily used in said field, e.g., water.

The dosage for a particular patient is determined according to age, body weight, general health conditions, sex, diet, administration time, administration method, excretion rate, drug combination, and severity of the illness being treated, in consideration of those or other factors.

The compounds and salts thereof represented by general formula (I) can be safely used at low toxicity level; the daily dose varies with patient condition, body weight, type of compound, administration route, etc.; e.g., non-orally, i.e. for subcutaneous, intravenous, intramuscular or intrarectal use, approximately 0.01–50 mg/person/day, preferably 0.01–20 mg/person/day, and orally, approximately 0.01–150 mg/person/day, preferably 0.1–100 mg/person/day, are recommended.

The invention is described in more detail with reference to examples. However, the invention is not limited to the specific embodiments.

EXAMPLE

Preparation Example

The prophylactic or therapeutic drug containing compound (I) or a salt thereof, referred to in the present invention as the active constituent for diabetic nephropathy or glomerular nephritis, for instance, can be manufactured according to the following formula:

1. Capsules

| (1) | 2-ethoxy-1-[[2'-(1H-tetrazole-5-yl)biphenyl-4-yl]methyl]-1H-benzimidazole-7-carboxylic acid | 10 mg |
|---|---|---|
| (2) | Lactose | 90 mg |
| (3) | Microcrystalline cellulose | 70 mg |
| (4) | Magnesium stearate | 10 mg |
|   | One capsule | 180 mg |

After (1) is mixed with (2), (3) and half of (4), the mixture is granulated. To the granules, the other half of (4) is added; the entire mixture is then sealed in a gelatin capsule.

2. Tablets

| (1) | 2-ethoxy-1-[[2'-(1H-tetrazole-5-yl)biphenyl-4-yl]methyl]-1H-benzimidazole-7-carboxylic acid | 10 mg |
|---|---|---|
| (2) | Lactose | 35 mg |
| (3) | Corn starch | 150 mg |
| (4) | Microcrystalline cellulose | 30 mg |
| (5) | Magnesium stearate | 5 mg |
|   | One tablet | 230 mg |

After (1) is mixed with (2), (3), ⅔ of (4) and half of (5), the mixture is granulated. To the granules, the remaining amounts of (4) and (5) are added; the mixture is then press-shaped into a tablet.

3. Injection

| (1) | 2-methylthio-1-[[2'-(1H-tetrazole-5-yl)biphenyl-4-yl]methyl]-1H-benzimidazole-7-carboxylic acid disodium salt | 10 mg |
|---|---|---|
| (2) | Inositol | 100 mg |
| (3) | Benzylalcohol | 20 mg |
|   | One ampule | 130 mg |

(1), (2) and (3) are dissolved in distilled water for injection to make the total volume 2 ml; the solution is sealed in an ampule. The entire process should be conducted under sterile conditions.

4. Capsules

| (1) | (±)-1-(cyclohexyloxycarbonyloxy)ethyl 2-ethoxy-1-[[2'-(1H-tetrazole-5-yl)biphenyl-4-yl]methyl]-1H-benzimidazole-7-carboxylate | 10 mg |
|---|---|---|
| (2) | Lactose | 90 mg |
| (3) | Microcrystalline cellulose | 70 mg |
| (4) | Magnesium stearate | 10 mg |
|   | One capsule | 180 mg |

After (1) is mixed with (2), (3) and half of (4), the mixture is granulated. To the granules, the other half of (4) is added; the entire mixture is then sealed in a gelatin capsule.

5. Tablets

| (1) | (±)-1-(cyclohexyloxycarbonyloxy)ethyl 2-ethoxy-1-[[2'-(1H-tetrazole-5-yl)biphenyl-4-yl]methyl]-1H-benzimidazole-7-carboxylate | 10 mg |
|---|---|---|
| (2) | Lactose | 35 mg |
| (3) | Corn starch | 150 mg |
| (4) | Microcrystalline cellulose | 30 mg |
| (5) | Magnesium stearate | 5 mg |
|   | One tablet | 230 mg |

After (1) is mixed with (2), (3), ⅔ of (4), and half of (5), the mixture is granulated. To the granules, the remaining amounts of (4) and (5) are added; the entire mixture is then press-shaped into a tablet.

6. Injection

| (1) | 2-ethoxy-1-[[2'-(1H-tetrazole-5-yl)biphenyl-4-yl]methyl]-1H-benzimidazole-7-carboxylic acid disodium salt | 10 mg |
|---|---|---|
| (2) | Inositol | 100 mg |
| (3) | Benzylalcohol | 20 mg |
|   | One ampule | 130 mg |

(1), (2) and (3) are dissolved in distilled water for injection to make the total volume 2 ml; the solution is then sealed in an ampule. The entire process should be conducted under sterile conditions.

7. Capsules

| | | |
|---|---|---|
| (1) | 2-butyl-1-[[2'-(1H-tetrazole-5-yl)biphenyl-4-yl]methyl]-1H-benzimidazole-7-carboxylic acid | 10 mg |
| (2) | Lactose | 90 mg |
| (3) | Microcrystalline cellulose | 70 mg |
| (4) | Magnesium stearate | 10 mg |
| | One capsule | 180 mg |

After (1) is mixed with (2), (3) and half of (4), the mixture is granulated. To the granules, the other half of (4) is added; the entire mixture is then sealed in a gelatin capsule.

8. Tablets

| | | |
|---|---|---|
| (1) | 2-butyl-1-[[2'-(1H-tetrazole-5-yl)biphenyl-4-yl]methyl]-1H-benzimidazole-7-carboxylic acid | 10 mg |
| (2) | Lactose | 35 mg |
| (3) | Corn starch | 150 mg |
| (4) | Microcrystalline cellulose | 30 mg |
| (5) | Magnesium stearate | 5 mg |
| | One tablet | 230 mg |

After (1) is mixed with (2), (3), ⅔ of (4) and half of (5), the mixture is granulated. To the granules, the remaining amounts of (4) and (5) are added; the mixture is then press-shaped into a tablet.

9. Capsules

| | | |
|---|---|---|
| (1) | Pivaloyloxymethyl 2-butyl-1-[[2'-(1H-tetrazole-5-yl)biphenyl-4-yl]methyl]-1H-benzimidazole-7-carboxylate | 10 mg |
| (2) | Lactose | 90 mg |
| (3) | Microcrystalline cellulose | 70 mg |
| (4) | Magnesium stearate | 10 mg |
| | One capsule | 180 mg |

After (1) is mixed with (2), (8) and half of (4), the mixture is granulated. To the granules, the other half of (4) is added; the entire mixture is then sealed in a gelatin capsule.

10. Tablets

| | | |
|---|---|---|
| (1) | Pivaloyloxymethyl 2-ethoxy-1-[[2'-(1H-tetrazole-5-yl)biphenyl-4-yl]methyl]-1H-benzimidazole-7-carboxylate | 10 mg |
| (2) | Lactose | 35 mg |
| (3) | Corn starch | 150 mg |
| (4) | Microcrystalline cellulose | 30 mg |
| (5) | Magnesium stearate | 5 mg |
| | Total | 230 mg per tablet |

Components (1), (2), (3), a two-thirds portion of component (4) and a half portion of component (5) were mixed and granulated. To these granules, the remaining portions of components (4) and (5) were added, and the whole mixture tableted by compressive tableting.

11. Capsules

| | | |
|---|---|---|
| (1) | 2-ethoxy-1-[[2'-(4,5-dihydro-5-oxo-1,2,4-oxadiazol-3-yl)biphenyl-4-yl]methyl]-1H-benzimidazole-7-carboxylic acid | 10 mg |
| (2) | Lactose | 90 mg |
| (3) | Microcrystalline cellulose | 70 mg |
| (4) | Magnesium stearate | 10 mg |
| | One capsule | 180 mg |

After (1) is mixed with (2), (3) and half of (4), the mixture is granulated. To the granules, the other half of (4) is added; the entire mixture is then sealed in a gelatin capsule.

12. Tablets

| | | |
|---|---|---|
| (1) | 2-ethoxy-1-[[2'-(4,5-dihydro-5-oxo-1,2,4-oxadiazol-3-yl)biphenyl-4-yl]methyl]-1H-benzimidazole-7-carboxylic acid | 10 mg |
| (2) | Lactose | 35 mg |
| (3) | Corn starch | 150 mg |
| (4) | Microcrystalline cellulose | 30 mg |
| (5) | Magnesium stearate | 5 mg |
| | One tablet | 230 mg |

After (1) is mixed with (2), (3), ⅔ of (4) and half of (5), the mixture is granulated. To the granules, the remaining mounts of (4) and (5) are added; the mixture is then press-shaped into a tablet.

The biologic activity of compounds and salts thereof possessing angiotensin-II-antagonistic action are described in Test Examples.

Test Example 1

Antiproteinuric action in rats with subtotally (5/6) nephrectomy (focal glomerulorsclerosis model; Meyer, T. W. and Renake, H. G.: Am. J. Physiol. 254, F856 (1988) or Yoshioka, T., Shiraga, H., Yoshida, Y., Fogo. A., Glick, A. D.: J. Clin. Invest. 82, 1614 (1988))

Compound 1: (±)-1-(cyclohexyloxycarbonyloxy)ethyl 2-ethoxy-1-[[2'-(1H-tetrazole-5-yl)biphenyl-4-yl]methyl]-1H-benzimidazole-7-carboxylate Method: Five-week-old male rats were anesthetized by intraperitoneal injection of pentobarbital sodium and ⅔ of the right kidney was removed. One week later, the entire left kidney was removed under similar anesthesia. After two-week breeding, 24-hour urine was collected and the total protein content and albumin content in the urine were determined by the use of A/G-B test (Wako Pure Chemistry Co., Ltd.). On the basis of urinary protein and blood pressure (BP), the rats were divided into two groups (vehicle-treated rats and rats treated with 1 mg/kg/day, p.o. of compound 1). Rats undergoing nephrectomy of the left kidney alone were also used as sham operated rats. Compound 1 was suspended in gum-arabic and the suspension was orally administered once a day for eight weeks. At the 2nd, 4th, 6th and 8th week of the treatment, 24-hour urine was collected.

Results: Table 1 summarizes the results. Urinary total protein and albumin began to markedly increase in vehicle-treated rats two weeks after surgery. Whereas, in rats treated with compound 1, these parameters did not increase and each parameter was rather significantly low six to eight weeks after the beginning of administration as compared with vehicle-treated rats. Since compound 1 suppresses aggravation of renal impairment, its efficacy in glomerulonephritis or diabetic nephropathy is expected.

TABLE 1

Antiproteinuric Action in subtotally (⅚) nephrectomized Rats

| | | Pre-administration | 2 weeks after the first dose | 4 weeks after the first dose | 6 weeks after the first dose | 8 weeks after the first dose |
|---|---|---|---|---|---|---|
| Urinary total protein (mg/100 g/ 24 hr) | Vehicle (n = 8–9) | 33.1 ± 3.1 | 36.4 ± 5.2 | 39.4 ± 4.8 | 35.3 ± 6.1 | 55.1 ± 9.1 |
| | Compound 1 (n = 9) | 32.8 ± 5.4 | 30.9 ± 5.2 | 27.7 ± 4.0 | 17.6 ± 5.6* | 24.4 ± 2.7** |
| | Shams (n = 6) | 9.7 ± 0.7 | 14.9 ± 1.5 | 13.1 ± 1.4 | 8.3 ± 0.5 | 11.9 ± 1.3 |
| Urinary albumin (mg/100 g/ 24 hr) | Vehicle (n = 8–9) | 7.7 ± 2.6 | 12.0 ± 3.1 | 14.1 ± 3.0 | 15.1 ± 3.7 | 24.5 ± 7.1 |
| | Compound 1 (n = 9) | 7.3 ± 2.3 | 6.3 ± 2.9 | 6.8 ± 3.4* | 7.4 ± 4.0* | 5.6 ± 2.7** |
| | Shams (n = 6) | 2.1 ± 0.2 | 1.9 ± 0.2 | 2.1 ± 0.2 | 1.3 ± 0.2 | 1.6 ± 0.2 |

Values are expressed as mean ± standard error.
Significance difference testing between controls and compound-1-treated rats or shams:
*$P < 0.05$
**$P < 0.01$

Test Example 2

Antiproteinuric action in rats with non-insulin-dependent (NIDD) diabetes (Wistar fatty rats) (Ikeda, H., Shino, A., Matsuo, T., Iwatsuka, H., and Suzuoki, Z.: Diabetes, 30, 1045 (1981) or Kava, R. A., West, D. B., Lukasik, V. A., and Greenwood, M. R. C: Diabetes, 38, 159 (1989)
Compound 1: (±)-1-(cyclohexyloxycarbonyloxy)ethyl 2-ethoxy-1-[[2'-(1H-tetrazole-5-yl)biphenyl-4-yl]methyl]-1H-benzimidazole-7-carboxylate Method: On the basis of blood glucose level and urinary protein content, 11-week-old Wistar fatty rats were divided into two groups (vehicle-treated rats and rats treated with 1 mg/kg/day, p.o. of compound 1). Non-diabetic control rats (lean rats) were also used. Compound 1 was suspended in gum-arabic and the suspension was orally administered once a day for ten weeks. At the 2nd, 4th, 6th, 8th and 10th week of the treatment, 24-hour urine was collected. The urine was centrifuged at 3,000 rpm and a portion of the supernatant was desalted on a column (Pharmacia PD10). Urinary total protein content and albumin content were determined by Lowry and ELISA methods, respectively.

Results: Table 2 summarizes the results. Urinary total protein content increased in vehicle-treated rats to about three times of the value in lean rats. This increase, however, was reduced to 1.2–1.5 times by the treatment with compound 1. Urinary albumin content also increased in vehicle-treated rats to about 100 times of the value in lean rats. This increase, however, was reduced to 20–30 times by the treatment with compound 1. Compound 1 did not affect blood glucose level. In non-insulin-dependent diabetic models, compound 1 is expected to be effective against diabetic nephropathy by decreasing the urinary protein without affecting the blood glucose level.

TABLE 2

Antiproteinuric Action in Rats with non-insulin-dependent diabetes

| | | age | | | | | |
|---|---|---|---|---|---|---|---|
| | | 11 weeks | 13 weeks | 15 weeks | 17 weeks | 19 weeks | 21 weeks |
| Urinary total protein (mg/24 hr) | vehicle (n = 6) | 101 ± 5 | 94 ± 14 | 118 ± 16 | 135 ± 15 | 117 ± 15 | 143 ± 22 |
| | Compound 1 (n = 6) | 101 ± 6 | 69 ± 11 | 91 ± 12 | 97 ± 11* | 79 ± 10* | 74 ± 13* |
| | Lean (n = 6) | 55 ± 2 | 36 ± 3 | 51 ± 3 | 51 ± 3 | 45 ± 2 | 45 ± 2 |
| Urinary albumin (mg/24 hr) | vehicle (n = 6) | 2.9 ± 0.4 | 24.6 ± 7.5 | 42.7 ± 9.0 | 46.4 ± 10.4 | 38.6 ± 6.4 | 28.6 ± 5.2 |
| | Compound 1 (n = 6) | 6.5 ± 4.1 | 11.2 ± 3.9 | 14.8 ± 6.1* | 21.8 ± 8.2 | 10.7 ± 3.9* | 15.4 ± 3.7* |
| | Lean (n = 6) | 0.4 ± 0.02 | 0.4 ± 0.04 | 0.6 ± 0.05 | 0.7 ± 0.08 | 0.6 ± 0.04 | 0.4 ± 0.03 |

Values are expressed as mean ± standard error. Figures in parentheses denote the number of rats.
Significance difference testing between controls and compound-1-treated or lean rats:
*$P < 0.05$.

Test Example 3

Acute Toxicity Test
Compound 1: (±)-1-(cyclohexyloxycarbonyloxy)ethyl 2-ethoxy-1-[[2'-(1H-tetrazole-5-yl)biphenyl-4-yl]methyl]-1H-benzimidazole-7-carboxylate The $LD_{50}$ of compound 1 is 2,000 mg/kg or more for 4-week-old Jcl:ICR mice (males and females) and for 5-week-old Jcl:Wister rats (males and females) via single oral administration.

What is claimed is:

1. A method for the treatment of sclerosis of the glomeruli in a mammal which comprises administering to said mammal a pharmaceutically effective amount of (±)-1-(cyclohexyl-oxycarbonyloxy) ethyl 2-ethoxy-1-[[2'-(1H-tetrazol-5-yl)-biphenyl-4-yl]methyl]-1H-benzimidazole-7-carboxylate or pharmaceutically acceptable salt thereof.

* * * * *